(12) United States Patent
Auger et al.

(10) Patent No.: US 9,209,003 B2
(45) Date of Patent: Dec. 8, 2015

(54) QUANTIFICATION OF AN ANALYTE IN SERUM AND OTHER BIOLOGICAL MATRICES

(71) Applicants: DH TECHNOLOGIES DEVELOPMENT PTE. LTD., Singapore (SG); PHYTRONIX TECHNOLOGIES INC., Québec (CA)

(72) Inventors: Serge Auger, Lévis (CA); Gregory Blachon, Québec (CA); Hesham Ghobarah, Oakville (CA); Michael Jarvis, Alliston (CA); Pierre Picard, Québec (CA)

(73) Assignees: DH TECHNOLOGIES DEVELOPMENT PTE. LTD., Singapore (SG); PHYTRONIX TECHNOLOGIES INC. (CA)

( * ) Notice: Subject to any disclaimer, the term of this patent is extended or adjusted under 35 U.S.C. 154(b) by 0 days.

(21) Appl. No.: 14/354,313

(22) PCT Filed: Oct. 26, 2012

(86) PCT No.: PCT/IB2012/002158
§ 371 (c)(1),
(2) Date: Apr. 25, 2014

(87) PCT Pub. No.: WO2013/061146
PCT Pub. Date: May 2, 2013

(65) Prior Publication Data
US 2014/0291505 A1  Oct. 2, 2014

Related U.S. Application Data

(60) Provisional application No. 61/711,871, filed on Oct. 10, 2012, provisional application No. 61/551,489, filed on Oct. 26, 2011.

(51) Int. Cl.
*H01J 49/04* (2006.01)
*G01N 33/82* (2006.01)
(Continued)

(52) U.S. Cl.
CPC ............ *H01J 49/0031* (2013.01); *G01N 33/82* (2013.01); *H01J 49/0431* (2013.01); *H01J 49/0445* (2013.01); *H01J 49/0463* (2013.01); *H01J 49/168* (2013.01); *G01N 27/624* (2013.01)

(58) Field of Classification Search
CPC .............. G01N 27/624; G01N 27/622; G01N 30/7206; G01N 30/30; G01N 30/461; G01N 30/462; G01N 30/54; G01N 30/6095; G01N 30/7233; G01N 33/0037; G01N 33/82; G01N 1/2214; G01N 1/405; H01J 49/0031; H01J 49/0463; H01J 49/165; H01J 49/168; H01J 49/004; H01J 49/0045; H01J 49/04; H01J 49/049; H01J 49/0027; H01J 49/0409; H01J 49/0418; H01J 49/0431; H01J 49/107; H01J 49/164; H01J 49/36; H01J 49/40; H01J 49/421; H01J 49/0018; H01J 49/0022; H01J 49/0081; H01J 49/025; H01J 49/0422; H01J 49/0445; H01J 49/0454; H01J 49/06; H01J 49/26; H01J 49/42; H01J 49/4215; H01J 49/422; H01J 49/424; H01J 49/4255; H01J 49/427; H01J 49/4285
USPC ......... 250/282, 281, 288, 287, 292, 290, 283, 250/286, 293, 291, 423 R, 424, 458.1, 200, 250/252.1, 289, 294, 310
See application file for complete search history.

(56) References Cited

U.S. PATENT DOCUMENTS 5,777,324 A * 7/1998 Hillenkamp ............... 250/288
6,423,966 B2 * 7/2002 Hillenkamp et al. ........ 250/288
(Continued)

OTHER PUBLICATIONS

Voislav Blagojevic et al: "Differential Mobility Spectrometry of Isomeric Protonated Dipeptides: Modifier and Field Effects on Ion Mobility and Stability", Analytical Chemistry, vol. 83, No. 9, May 2011, pp. 3470-3476.
(Continued)

*Primary Examiner* — David A Vanore (57) ABSTRACT

Methods and systems for quantifying analytes in a biological sample are provided comprising preparing a biological sample for mass spectrometric analysis, utilizing an ionization source to ionize at least a portion of the prepared biological sample to generate an ionized analyte flow, introducing the ionized analyte flow into a differential mobility spectrometer set at a compensation voltage selected to extract ionized analyte molecules from the ionized analyte flow, introducing an output analyte flow of the differential mobility spectrometer into a mass spectrometer to detect and quantify analyte ions in the output analyte flow.

22 Claims, 11 Drawing Sheets

(51) Int. Cl.
*H01J 49/36* (2006.01)
*H01J 49/00* (2006.01)
*H01J 49/16* (2006.01)
G01N 27/62 (2006.01)

(56) References Cited

U.S. PATENT DOCUMENTS

| | | | | |
|---|---|---|---|---|
| 6,797,945 | B2* | 9/2004 | Berggren et al. | 250/288 |
| 7,019,291 | B2* | 3/2006 | Miller et al. | 250/292 |
| 7,518,108 | B2* | 4/2009 | Frey et al. | 250/288 |
| 7,579,589 | B2* | 8/2009 | Miller et al. | 250/292 |
| 7,608,818 | B2* | 10/2009 | Miller et al. | 250/288 |
| 7,858,927 | B2* | 12/2010 | Thomson | 250/281 |
| 7,880,140 | B2* | 2/2011 | Guna et al. | 250/292 |
| 8,101,910 | B2* | 1/2012 | Loboda | 250/292 |
| 8,173,959 | B1* | 5/2012 | Boumsellek et al. | 250/288 |
| 8,217,345 | B2* | 7/2012 | Thomson | 250/294 |
| 8,350,212 | B2* | 1/2013 | Covey et al. | 250/281 |
| 8,440,968 | B2* | 5/2013 | Giles | 250/292 |
| 8,610,058 | B2* | 12/2013 | Verbeck et al. | 250/288 |
| 8,884,219 | B2* | 11/2014 | Boulbitch | 250/287 |
| 8,946,626 | B2* | 2/2015 | Giles et al. | 250/292 |
| 8,975,578 | B2* | 3/2015 | Green et al. | 250/283 |
| 2006/0054807 | A1* | 3/2006 | Picard et al. | 250/288 |
| 2007/0272852 | A1* | 11/2007 | Miller et al. | 250/288 |
| 2008/0173809 | A1 | 7/2008 | Wu | |
| 2008/0177359 | A1* | 7/2008 | Pierce | 607/103 |
| 2009/0084979 | A1* | 4/2009 | DeWalch | 250/458.1 |
| 2009/0218481 | A1* | 9/2009 | DeWalch | 250/281 |
| 2009/0294650 | A1 | 12/2009 | Schneider et al. | |
| 2009/0317916 | A1* | 12/2009 | Ewing et al. | 436/153 |
| 2010/0200742 | A1* | 8/2010 | Schultz et al. | 250/252.1 |
| 2011/0042561 | A1* | 2/2011 | Miller et al. | 250/282 |
| 2011/0133069 | A1 | 6/2011 | Holmquist et al. | |
| 2011/0174964 | A1* | 7/2011 | Brunelli et al. | 250/282 |
| 2013/0306858 | A1* | 11/2013 | Giles et al. | 250/283 |
| 2014/0291505 | A1* | 10/2014 | Auger et al. | 250/282 |
| 2015/0008316 | A1* | 1/2015 | Guna | 250/283 |
| 2015/0076342 | A1* | 3/2015 | Campbell et al. | 250/288 |

OTHER PUBLICATIONS

Eiceman G A et al: "Separation of Ions From Explosives in Differential Mobility Spectrometry by Vapor-Modified Drift Gas", Analytical Chemistry, vol. 76, No. 17, Sep. 2004, pp. 4937-4944.
Tadjimukhamedov F K et al: "Evaluation of a Differential Mobility Spectrometer/Miniature Mass Spectrometer System", Journal of the American Society for Mass Spectrometry, vol. 21, No. 9, Sep. 2010, pp. 1477-1481.
Abu B. Kanu et al: "Ion mobility-mass spectrometry", Journal of Mass Spectrometry, vol. 43, No. 1, Jan. 2008, pp. 1-22.
Alex Birsan, Laser Diode Thermal Desoprtion (LDTD) in Toxicology, Retrieved from the Internet:http://www.arcsciences.com/Editor/assets/phytronix/brochures apps and ppts/ldtd ion source_forensic applications_small.pdf (retrieved Jul. 8, 2015).

* cited by examiner

| Expected Concentration | Mean Calculated Concentration | % CV | Standard Deviation | % Accuracy |
|---|---|---|---|---|
| 0.10 | 1.062e-1 | 16.67 | 1.770e-2 | 106.16 |
| 1.00 | 1.013e0 | 9.39 | 9.509e-2 | 101.25 |
| 10.00 | 9.406e0 | 7.28 | 6.850e-1 | 94.06 |
| 100.00 | 9.830e1 | 3.86 | 3.790e0 | 98.30 |
| 1000.00 | 1.002e3 | 2.23 | 2.234e1 | 100.23 |

QUANTIFICATION OF AN ANALYTE IN SERUM AND OTHER BIOLOGICAL MATRICES

RELATED APPLICATIONS

This application claims priority to U.S. provisional application No. 61/551,489 filed Oct. 26, 2011, which is incorporated herein by reference in its entirety, and this application claims priority to U.S. provisional application No. 61/711,871 filed Oct. 10, 2012, which is incorporated herein by reference in its entirety.

FIELD

The invention relates generally to methods and systems for detecting and quantifying analytes in samples, such as serum and other biological samples, using mass spectrometry.

BACKGROUND

Mass spectrometric detection and quantification of analytes contained within complex matrices generally requires high resolution separation techniques to reduce the effect of interfering species within the sample. By way of example, most mass spectrometric analyses utilize liquid chromatographic separation techniques to improve selectivity of the downstream spectrometric detection of the analyte of interest. Though such separation techniques can lead to more accurate quantification, sample preparation and chromatographic separation can be both time consuming and costly, thereby reducing throughput.

Accordingly, there is a need for methods and systems having increased throughput, while allowing for the selective detection and quantification of analytes of interest in complex biological sample, e.g., testosterone and Vitamin D in serum.

SUMMARY

According to various embodiments, methods and systems for detecting and/or quantifying analytes in a sample using mass spectrometry are provided herein. As described below, these methods and systems can enable the detection and/or quantification of analytes in complex matrices without the use of time-consuming separation techniques. By way of example, the concentration of testosterone and Vitamin D in multiple biological samples (e.g., serum) can be rapidly quantified utilizing laser desorption thermal ionization in combination with differential mobility spectrometry. In various embodiments, the analyte can comprise 25-OH-Vitamin D3. In various embodiments, the analyte can comprise 25-OH-Vitamin D2. In various embodiments, the ion mobility spectrometer can comprise for example, a differential mobility spectrometer (DMS), FAIMS devices of various geometries, such as parallel plate, curved electrode, or cylindrical FAIMS device, among others. In many embodiments, this can be performed without the use of liquid chromatographic separation techniques prior to ionization.

According to various embodiments, a method of quantifying an analyte in a biological sample is disclosed. The method includes preparing a biological sample for mass spectrometric analysis and utilizing an ionization source to ionize at least a portion of the prepared biological sample to generate an ionized analyte flow. The ionized analyte flow is introduced into a differential mobility spectrometer set at a compensation voltage selected to extract ionized analyte molecules from the ionized analyte flow, and the output analyte flow of the differential mobility spectrometer is introduced into a mass spectrometer to detect and quantify analyte ions in said output analyte flow. In various embodiments, the analyte can comprise testosterone. In various embodiments, the analyte can comprise Vitamin D. In various embodiments, the analyte can comprise 25-OH-Vitamin D3. In various embodiments, the analyte can comprise 25-OH-Vitamin D2.

In one aspect, the ionization source can include a laser diode thermal desorption (LDTD) ionization source. In some embodiments, the ionization source can include a diode laser to impart heat energy to a prepared biological sample to desorb at least a portion of the biological sample. In a related aspect, the ionization source can include an APCI ionizer for ionizing the desorbed biological sample.

In various aspects, the mass spectrometer can comprise a tandem mass spectrometer. For example, the tandem mass spectrometer can be a triple quadrupole mass spectrometer. In one aspect, the method can include detecting at least one precursor-product ion pair transitions having an m/z value of about 289/97, 289/109, and 292/97. In one aspect, the method can include detecting at least one precursor-product ion pair transitions having an m/z value of about 401.3/365.2, 401.3/257.1, and 401.3/201.1. In various embodiments, the method can include detecting at least one precursor-product ion pair transitions having an m/z value of about 413.3/355.2 and 413.3/337.2.

The differential mobility spectrometer can have a variety of configurations. For example, the compensation voltage can be about 4 volts. In such a manner, the differential mobility spectrometer can preferentially transmit testosterone, for example. In various embodiments, the compensation voltage can be in the range of about 4 volts to about 12 volts. In various aspects, the compensation voltage can be in the range of about 4 volts to about 14 volts.

In some aspects, the biological sample can be prepared without liquid chromatographic separation. In a related aspect, the sample can be prepared by performing liquid-liquid extraction and drying the biological sample prior to the ionizing step. In some embodiments, the ionization source can rapidly ionize multiple samples. For example, within about 10 seconds of ionizing a first biological sample, the ionization source can ionize at least a portion of an additional prepared biological sample to generate an additional ionized analyte flow. In various embodiments, the biological sample can be disposed on a sample plate of the ionization source. The biological sample can be, for example, dry.

In some aspects, the biological sample could be one of blood, plasma, serum, oral fluid, and urine. In some embodiments, analytes in the biological sample can be detected at a quantitation limit of about 0.1 ng/mL. In other words, the methods described herein can be capable of detecting a concentration of analyte as low as 0.1 ng/mL in a biological sample. In various embodiments, the analyte can comprise testosterone. In various embodiments, the analyte can comprise Vitamin D. In various embodiments, the analyte can comprise 25-OH-Vitamin D3. In various embodiments, the analyte can comprise 25-OH-Vitamin D2.

In one aspect, a mass spectrometry system is disclosed. The system includes an ionization source having a heat source configured to apply heat to a sample to cause desorption of at least a portion of the sample and an ionizer for ionizing at least a part of the desorbed portion to generate an ionized sample. The system also includes a differential mobility spectrometer in communication with the ionization source. The differential mobility spectrometer can receive at least a portion of the ionized sample from the ionization source and transmit ions of a selected differential mobility. A mass spectrometer, in communication with the differential mobility spectrometer, is configured to analyze said ions of the selected differential mobility received from the differential mobility spectrometer. In various embodiments, the analyte can comprise testosterone. In various embodiments, the analyte can comprise Vitamin D. In various embodiments, the analyte can comprise 25-OH-Vitamin D3. In various embodiments, the analyte can comprise 25-OH-Vitamin D2.

In some embodiments, the heat source can include a laser diode. For example, the laser diode can be configured to generate a laser beam directed to a sample well containing the sample.

The ionizer can have a variety of configurations to generate an ionized sample. In various embodiments, the ionizer can include an atmospheric pressure chemical ionization source. In one aspect, the ionizer comprises an ionizing needle generating a corona discharge. In another aspect, the ionizer can include an ultraviolet light source configured to generate a light beam for ionizing said desorbed sample by photo-ionization. In various embodiments, the mass spectrometer can comprise a tandem mass spectrometer. In various aspects, the mass spectrometer can be a triple quadrupole mass spectrometer. In various aspects, the system can detect at least one precursor-product ion pair transitions having an m/z value of about 289/97, 289/109, and 292/97. In various aspects, the system can detect at least one precursor-product ion pair transitions having an m/z value of about 401.3/365.2, 401.3/257.1, and 401.3/201.1. In various embodiments, the system can detect at least one precursor-product ion pair transitions having an m/z value of about 413.3/355.2 and 413.3/337.2. In various embodiments, the differential mobility spectrometer can have a variety of configurations. For example, the compensation voltage can be about 4 volts. In such a manner, the differential mobility spectrometer can preferentially transmit testosterone, for example. In various embodiments, the compensation voltage can be in the range of about 4 volts to about 12 volts. In various aspects, the compensation voltage can be in the range of about 4 volts to about 14 volts.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

Those skilled in the art will understand that the methods and systems described herein are non-limiting exemplary embodiments and that the scope of the applicants' disclosure is defined solely by the claims. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of ordinary skill in the art. The features illustrated or described in connection with one exemplary embodiment may be combined with the features of other embodiments. Such modifications and variations are intended to be included within the scope of the applicants' disclosure.

Figure 1:
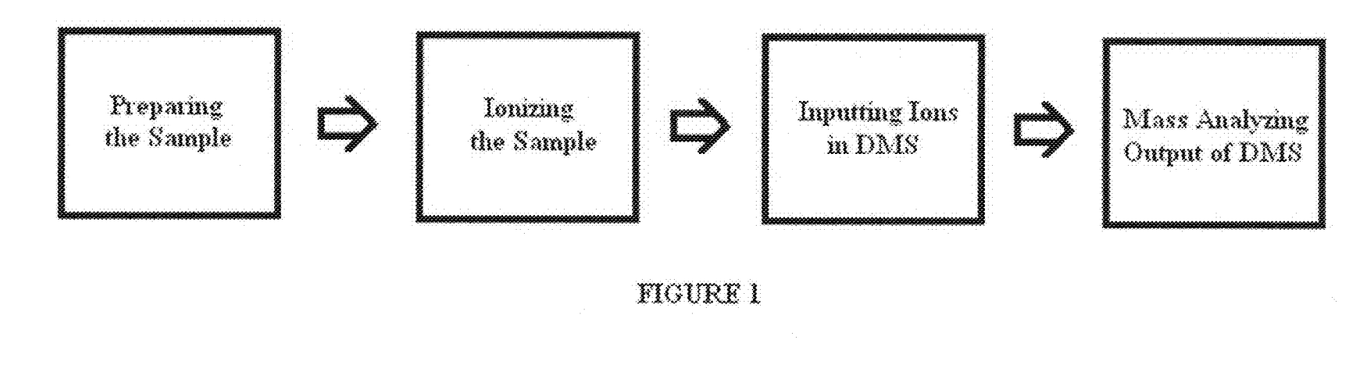
FIG. 1 exemplifies a method for quantifying an analyte in accordance with various embodiments of the applicant's teachings.

According to various embodiments, methods are provided for quantifying an analyte of interest in a biological sample. FIG. 1 depicts one exemplary embodiment of a method for quantifying an analyte, according to Applicant's teachings. As shown, the method can include preparing a biological sample, ionizing the sample, inputting ions into the differential mobility spectrometer (DMS), and mass analyzing the output of the DMS.

As will be appreciated by the person skilled in the art, samples containing or suspected of containing an analyte of interest can be prepared for mass spectrometric analysis. By way of example, the sample can be a biological sample such as blood, serum, plasma, oral fluid, or urine. The sample can be prepared using a variety of techniques known in the art modified in accord with the teachings herein. In some embodiments, methods in accordance with the Applicant's teachings can eliminate time-consuming sample preparation steps. For example, in some embodiments, preparing the sample need not include using liquid chromatography to separate potentially interfering species present in the sample. In one aspect, sample preparation can include performing liquid-liquid extraction and drying, as discussed herein.

The prepared sample can then be ionized. Various ionization techniques known in the art and modified in accord with the teachings herein can be used to ionize the prepared sample. In one embodiment, laser diode thermal desorption can be used to sequentially ionize multiple samples, as discussed herein. In an exemplary embodiment, a prepared sample disposed on a sample plate, for example, can be desorbed through irradiation of the sample plate (e.g., a portion in thermal contact with the sample) or the sample itself to vaporize a portion of the sample. The desorbed portion of the sample can be transmitted to an ionizer to ionize the desorbed sample. As will be appreciated by a person skilled in the art, various ionization techniques, modified in accord with the teachings herein, can be utilized to ionize the sample. By way of example, atmospheric pressure chemical ionization or photo-ionization can be used to ionize a part of the desorbed sample.

After being ionized, a portion of the sample can be delivered to a differential mobility spectrometer to at least partially extract a selected ionized analyte from the ionized sample. As will be appreciated by a person skilled in the art, the compensation voltage of the differential mobility spectrometer can be selected to preferentially transmit the analyte of interest. By way of example, the compensation voltage can be set at about 4 volts to preferentially transmit ionized testosterone to a downstream mass analyzer. In various embodiments, the compensation voltage can be in the range of about 4 volts to about 12 volts. In various aspects, the compensation voltage can be in the range of about 4 volts to about 14 volts.

The ions exiting the DMS can be analyzed by a downstream mass spectrometer, such as a tandem mass spectrometer. As will be appreciated by a person skilled in the art, various techniques for analyzing the ions transmitted by the differential mobility spectrometer can be utilized. By way of example, selected MRM transitions can be observed for an analyte of interest to enable quantitation of the analyte in the sample. In one exemplary embodiment in which testosterone is detected and quantified, at least one product-precursor ion pair transitions having a m/z value of about 289/97, 289/109, and 292/97 can be used. In one exemplary embodiment in which 25-OH-Vitamin D3 is detected and quantified, at least one product-precursor ion pair transitions having a m/z value of about 401.3/365.2, 401.3/257.1, and 401.3/201.1 can be used. In one exemplary embodiment in which 25-OH-Vitamin D2 is detected and quantified, at least one product-precursor ion pair transitions having a m/z value of about 413.3/355.2 and 413.3/337.2 can be used.

Figure 2:
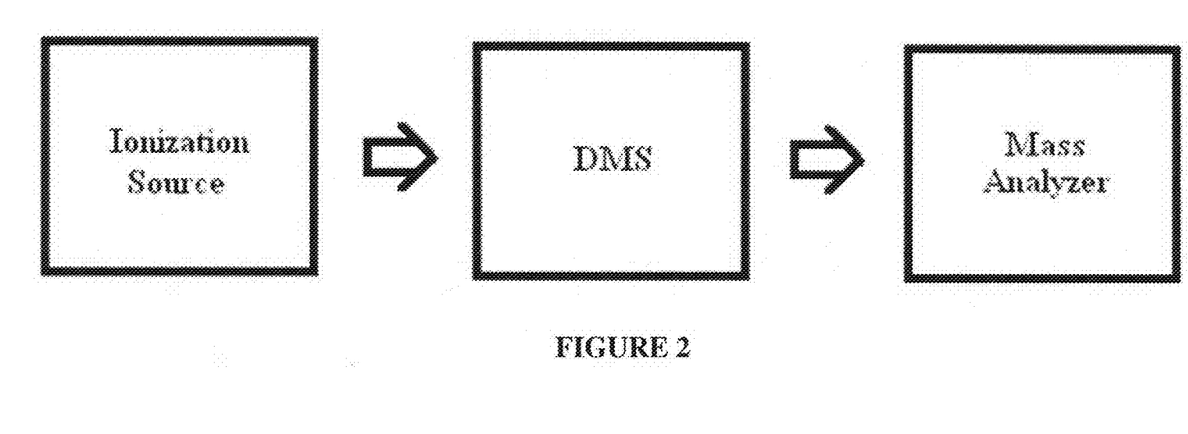
FIG. 2 exemplifies a system for quantifying an analyte in accordance with various embodiments of the applicant's teachings.

According to various embodiments, mass spectrometry systems are provided for quantifying an analyte of interest in a biological sample. FIG. 2 depicts one exemplary embodiment of a system for quantifying an analyte. As shown, the system includes an ionization source operatively coupled to a differential mobility spectrometer (DMS), and a downstream mass analyzer. As will be appreciated by a person skilled in the art, systems in accord with Applicant's teachings can be used to quantify a variety of analytes present in various biological samples, such as testosterone and Vitamin D. In various embodiments, the analyte can comprise 25-OH-Vitamin D3. In various embodiments, the analyte can comprise 25-OH-Vitamin D2.

As discussed herein, the sample can be prepared prior to ionization. Various ionization sources can then be used to ionize the sample. For example, APCI and photo-ionization sources can be used to ionize the sample. In one embodiment, the ionization source can be a laser diode thermal desorption ionization source, which can be effective to desorb and/or ionize the prepared sample. The LDTD S-960/S-3480 manufactured by Phytronix Technologies, Inc. of Quebec, Canada is one example of such a source that can operate as discussed, for example, as described below in the Examples section.

The ionized sample can then be transmitted to the DMS, which can selectively transmit an analyte of interest (e.g., testosterone, Vitamin D, etc.) to the downstream mass analyzer. In various embodiments, a chemical modifier can be introduced in the system, for example, in the DMS interface. Though the DMS and mass analyzer are depicted as separate components, a person skilled in the art will appreciate that the DMS can be implemented as an integrated unit. By way of example, the SelexION™ ion mobility device can be interfaced directly with a QTRAP® 5500 triple quadrupole mass spectrometer, as produced by AB SCIEX of Framingham, Mass. As will be appreciated by a person skilled in the art, the mass analyzer can have a variety of configurations and can be a standalone mass analyzer operatively coupled to the DMS. By way of example, the mass analyzer can be a tandem mass spectrometer, a triple quadrupole, QqTOF or trap-TOF mass spectrometer.

EXAMPLES

The applicants' teachings can be even more fully understood with reference to the examples and resulting data presented below. Other embodiments of the applicants' teachings will be apparent to those skilled in the art from consideration of the present specification and practice of the present teachings disclosed herein. It is intended that these examples be considered as exemplary only.

Figure 3:
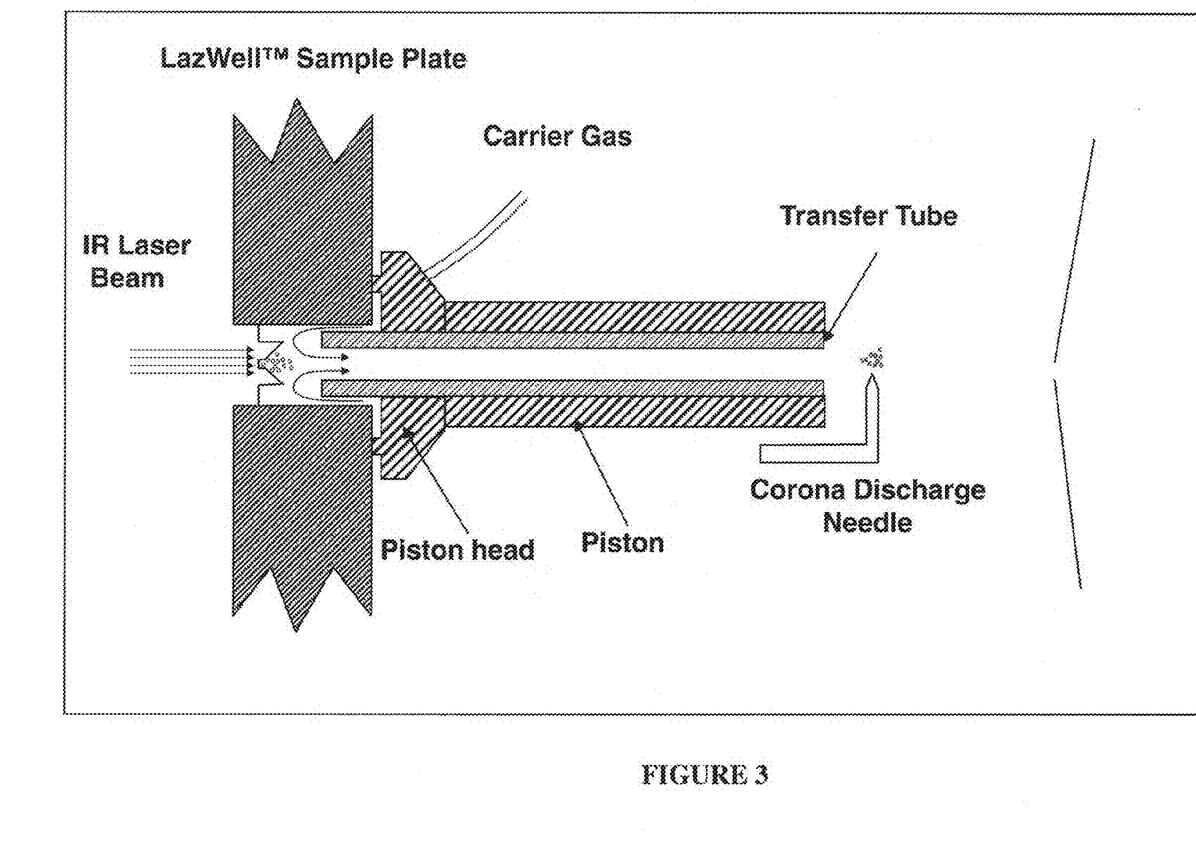
FIG. 3 shows a schematic of a laser diode thermal desorption (LDTD) ionization source in accordance with various embodiments of the applicant's teachings.

The Laser Diode Thermal Desorption (LDTD) ionization source technology was coupled to a mass spectrometer equipped with the SelexION™ differential ion mobility device, enabling a high throughput capacity for the analysis of an analyte in biological matrix. The LDTD source allowed a rapid laser thermal desorption of the sample at atmospheric pressure, followed by an APCI type ionization. The lower limit of quantitation for the LDTD-MS/MS analysis of analytes can be limited by the blank interference arising from the presence of isobaric analytes, however the addition of the SelexION™ differential ion mobility device between the LDTD source and the tandem mass spectrometer provided enhanced selectivity, and effectively allowed the separation of the isobaric analytes. FIG. 3 shows a schematic of the LDTD ionization source. The LDTD uses a Laser Diode to produce and control heat on the sample support which was a 96 well plate. The energy is then transferred through the sample holder to the dry sample which vaporizes prior to being carried by a gas in an APCI region. High efficiency protonation with strong resistance to ionic suppression characterize the ionization, due to the absence of solvent and mobile phase. This allowed very high throughput capabilities of 7 seconds sample-to-sample analysis time, without carry over. The SelexION™ ion mobility device enabled enhanced selectivity over traditional MS/MS analysis by providing an orthogonal means of separating isobaric species, using differential mobility spectrometry. This capability becomes especially important when liquid chromatography is not used to separate isobaric species prior to analysis by MS/MS. In the example, the ion mobility cell was interfaced directly to the front of a QTRAP® 5500 mass spectrometer, and was optimized for the detection of testosterone by tuning the Compensation Voltage (CoV) parameter to a value of 4 V.

Sample Preparation was as follows:
1. 100 µL of the serum sample was transferred to a borosilicate tube.
2. 20 µL of IS working stock solution (10 ng/mL) was added to each tube.
3. 300 µL of NaOH (IN) was pipetted into the borosilicate tube and mixed for 10 seconds using a vortex mixer.
4. 400 µL of MTBE was added to the tube and mixed for 30 seconds using a vortex mixer.
5. The tube was left to stand for 5 minutes at ambient temperature and centrifuged for 5 minutes at 14000 rpm.
6. 200 µL of the supernatant was transferred to a clean borosilicate tube and evaporated to dryness under N2 gas at 45° C.
7. Samples were reconstituted in 40 µL of reconstitution solution and mixed for 60 seconds using a vortex mixer.

8. The tube was then centrifuged at 14000 rpm for 1 minute to sediment any insoluble or particulate matter.
9. The clean precipitate-free solution was transferred to a borosilicate HPLC vial equipped with a 200 μL insert.

Figure 4:
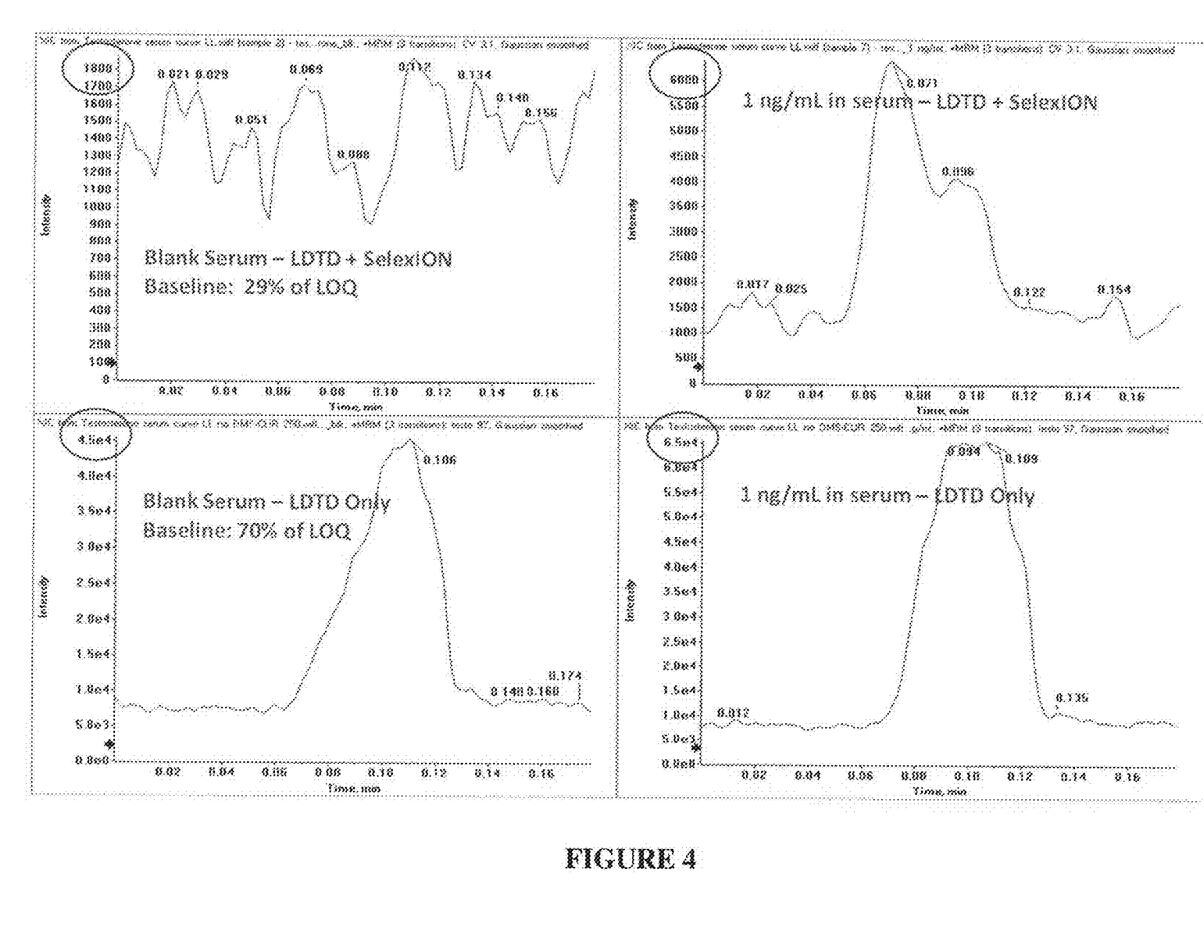
FIG. 4 shows the reduction of interference in the blank when the LDTD source and the ion mobility device were used in tandem to analyze spiked serum testosterone calibrators in accordance with various embodiments of the applicant's teachings.

As shown in FIG. 4, when the LDTD source and SelexION™ ion mobility device were used in tandem to analyze spiked serum testosterone calibrators, the interference in the blank was reduced from 65% to nearly zero, resulting in a 10× improvement in the lower limit of quantitation. Sample preparation consisted of a simple liquid-liquid extraction of human plasma using ethyl acetate, in a 1:4 v/v ratio. 2 μl of the upper layer was deposited directly into the 96 well plate and allowed to dry prior to analysis. These results represent a significant improvement over results obtained in the absence of the SelexION™ ion mobility device.

Figure 5:
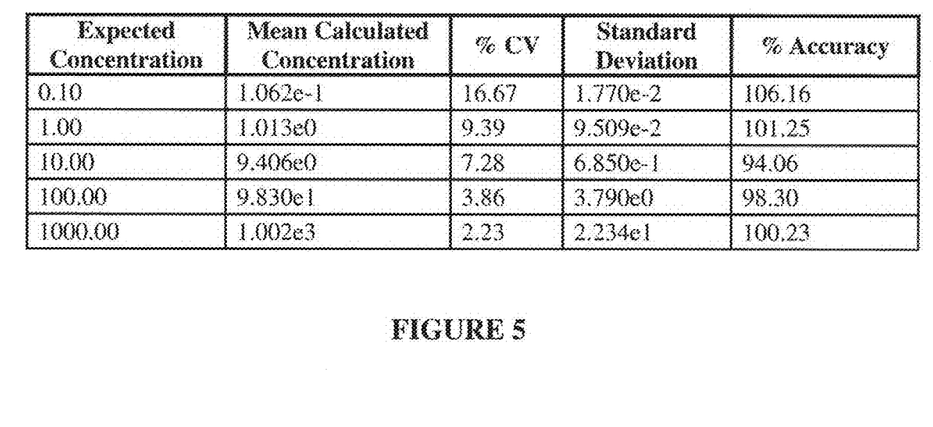
FIG. 5 shows accuracy and reproducibility in accordance with various embodiments of the applicant's teachings.

The lower limit of quantitation was 0.1 ng/ml, and the assay displayed excellent linearity, with r2=0.99972, over 5 orders of magnitude. Accuracy and reproducibility were within the accepted values as shown in FIG. 5. The sample-to-sample run time was only 7 seconds. In comparison, the equivalent analysis using conventional LC-MS/MS would typically require approximately 3-5 minutes per sample.

Results show that in L/L serum extracts, baseline is reduced significantly and to the point where achieving suitable LOQ's is feasible, as shown in FIG. 4. This was achieved without the introduction of a chemical modifier in the DMS interface. Under these conditions, testosterone has an optimum COV of 4 V. Additional selectivity may potentially be achieved by introducing modifiers.

Figure 6:
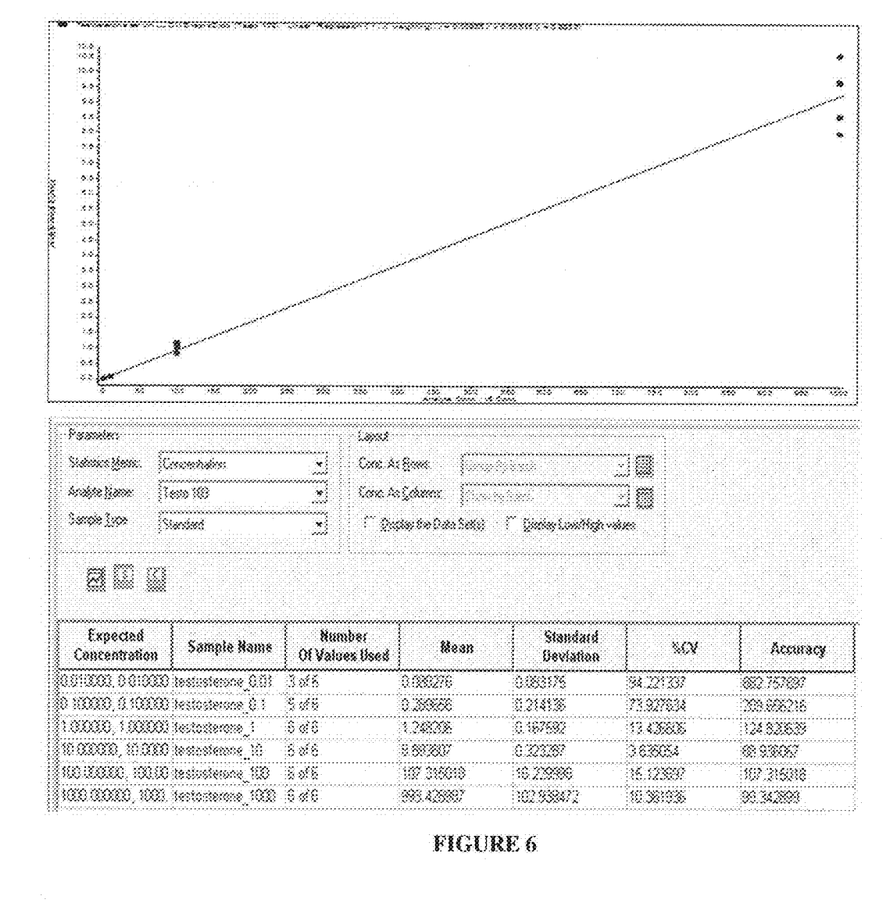
FIG. 6 shows standard curve results in accordance with various embodiments of the applicant's teachings.
Figure 7:
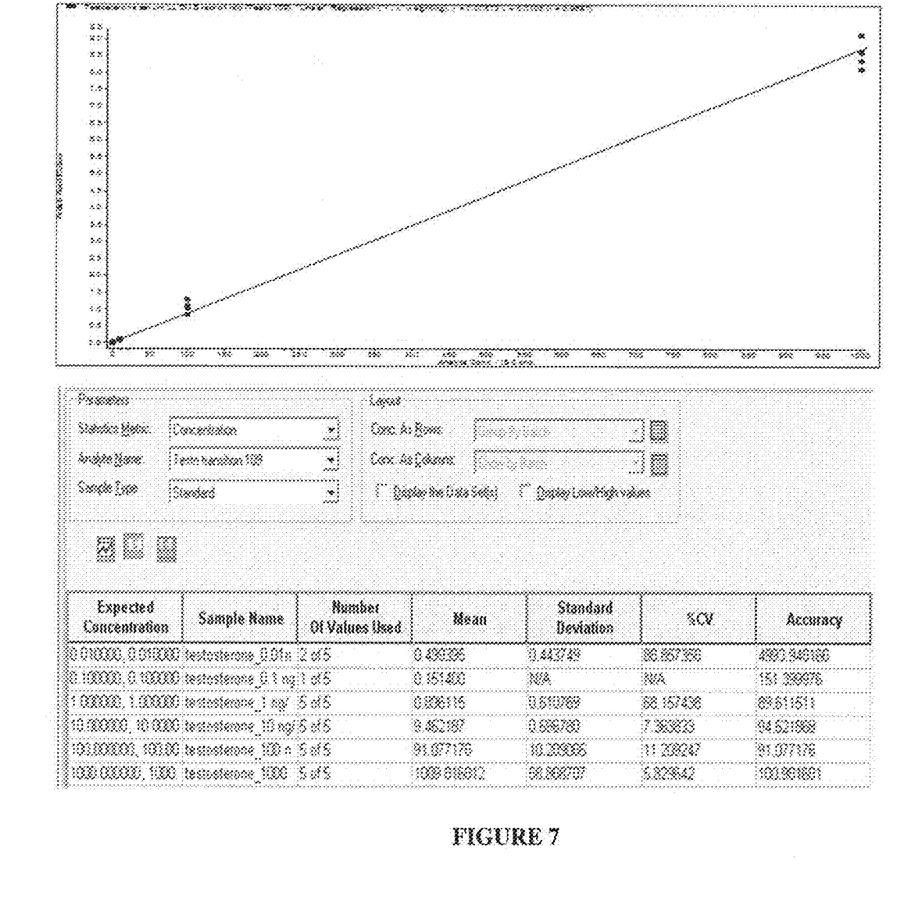
FIG. 7 shows standard curve results in accordance with various embodiments of the applicant's teachings.

Extracted spiked serum calibrants were spotted and analysed using the LDTD/SelexION™ combination. The experiment was repeated yielding two sets of standard curve results as shown in FIGS. 6 and 7. The results show good linearity.

The LDTD source and an ion mobility device, the SelexIon in this example, were used in tandem to analyze Vitamin D to separate the isobaric interference of 7-α-hydroxy-4-cholesten-3-one. The Laser Diode Thermal Desorption (LDTD) ionization source was coupled to a mass spectrometer equipped with the SelexION™ differential ion mobility cell, enabling a high throughput capacity for the analysis of 25-hydroxyvitamin D2 and D3 in biological matrix, with sample-to-sample analysis time of 9 seconds. Preparation of plasma sample consisted of a protein precipitation by addition of methanol followed by a liquid-liquid extraction with hexane. 5 μl of the upper layer is deposited in proprietary 96-wells plate and allowed to dry prior to analysis. The endogenous isobaric compound 7α-hydroxy-cholesten-3-one, known to interfere at the MS/MS transition of 25-OH-D3, was separated by the action of the Differential Mobility Spectrometer as demonstrated by specific desorption of individual standards. Calibration curve was prepared using a multilevel calibrator set from Chromsystem. Additional curve levels were prepared by dilution of calibrator with stripped serum. Multiple tests were conducted for validation. Matrix effect was evaluated by first measuring the original level of 6 different plasma samples and spiking them with a known amount of 25-OH-D3. Constant endogenous+spiked quantity was observed. Specificity was measured as the blank level peak area compared to the signal area at the limit of quantitation. Reproducibility was tested as intra-day and inter-day repeated measurements. Stability was evaluated in matrix, extract and dried onto Lazwell plate at room temperature and 4° Celsius. Finally, 6 concomitant drugs (Caffeine, Acetaminophen, etc.) were spiked in a QC to verify potential interferences. Quantitation ranged from 1-65 ng/ml and 1.5-94 ng/ml for 25-OH-vitamin D3 and D2 respectively. Blank levels were less than 20% of the LOQ for both compounds. To assess the accuracy and precision, calibration points and QC were analyzed in triplicate. Reproducibility for n=3 ranged from 0.6 to 12.3%. Calculated concentrations of QC were within 15% of the reported values. Correlation between LC MS/MS and LDTD MS/MS samples were expressed by $r^2$=0.952. Analyzing sample in 9 seconds with LDTD MS/MS met the guidelines of regulatory environment for all validation parameters.

Figure 8:
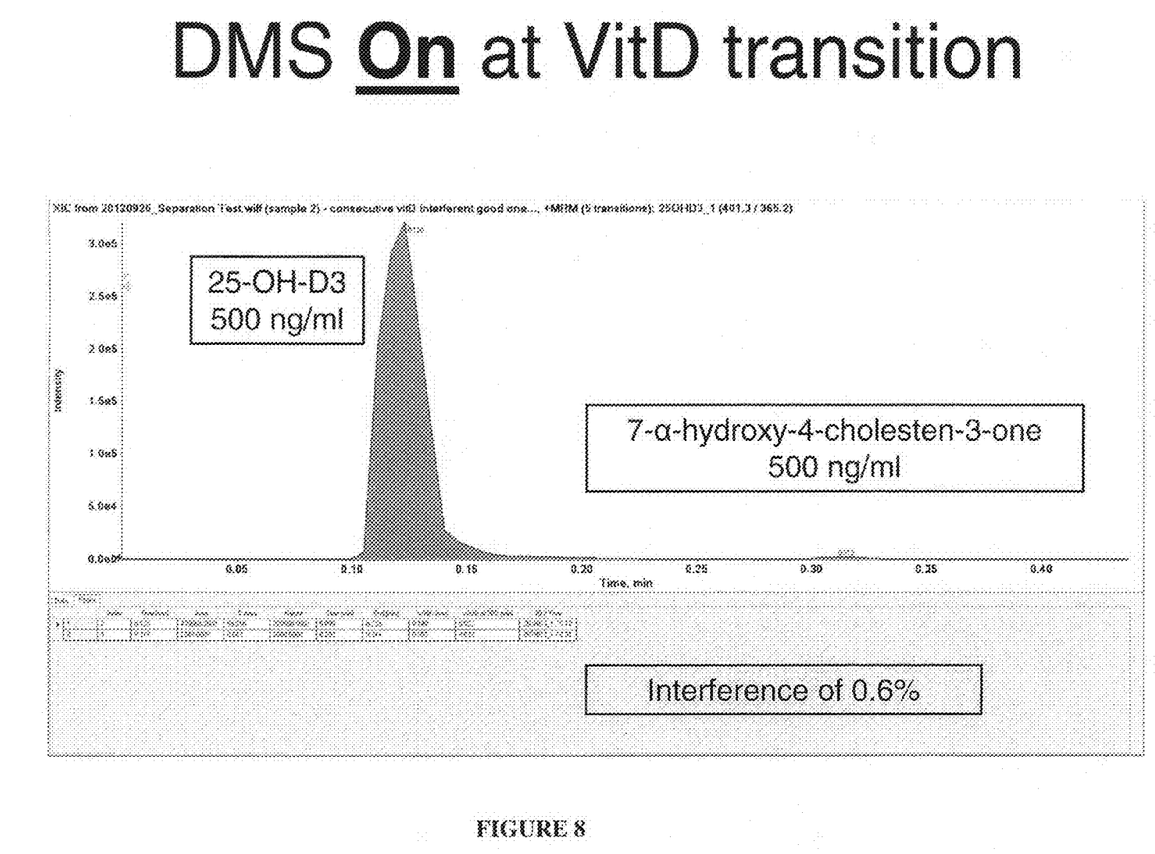
FIG. 8 shows the reduction of interference when the LDTD source and the ion mobility device were used in tandem to analyze Vitamin D in accordance with various embodiments of the applicant's teachings.
Figure 9:
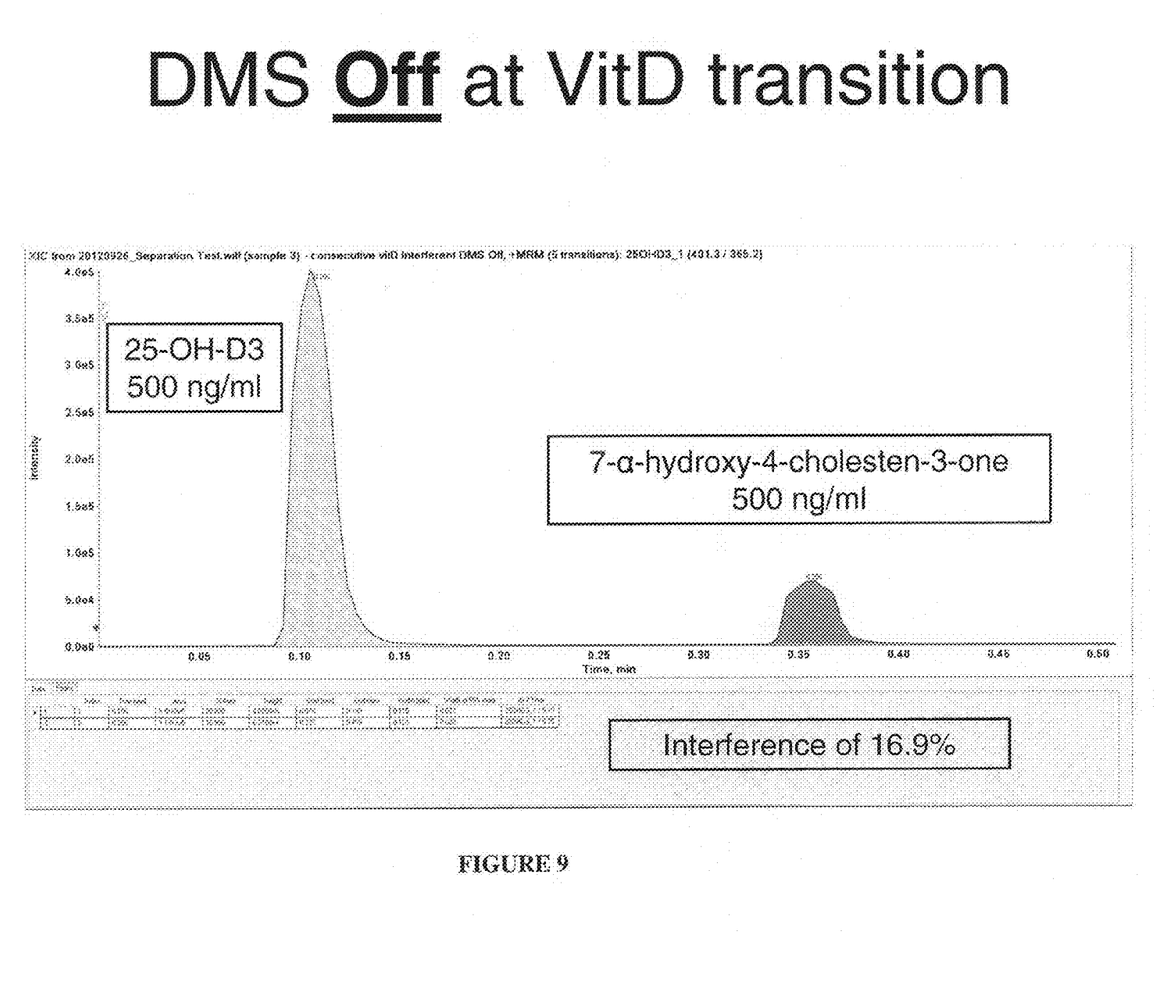
FIG. 9 shows the interference when only the LDTD source was used and the ion mobility device was turned off to analyze Vitamin D in accordance with various embodiments of the applicant's teachings.

Sample preparation was as follows:
Standard in plasma from Chromsystems
Blank from double stripped plasma: conc.<1 ng/ml
Serial dilution of plasma
Deuterated internal standard
20 μl of plasma crashed with 40 μl of MeOH
40 μl of supernatant+20 μl water NaCl saturated+40 μl Hexane
2 μl deposit As shown in FIG. 8, when the LDTD source and the ion mobility device, the differential mobility device SelexION™, in this example, was on and were used in tandem to analyze Vitamin D, the interference from 7-α-hydroxy-4-cholesten-3-one, interference was 0.6%. In contrast, as shown in FIG. 9, when only the LDTD source was used, and the differential mobility device was off, the interference from 7-α-hydroxy-4-cholesten-3-one was 16.9%.

Figure 10:
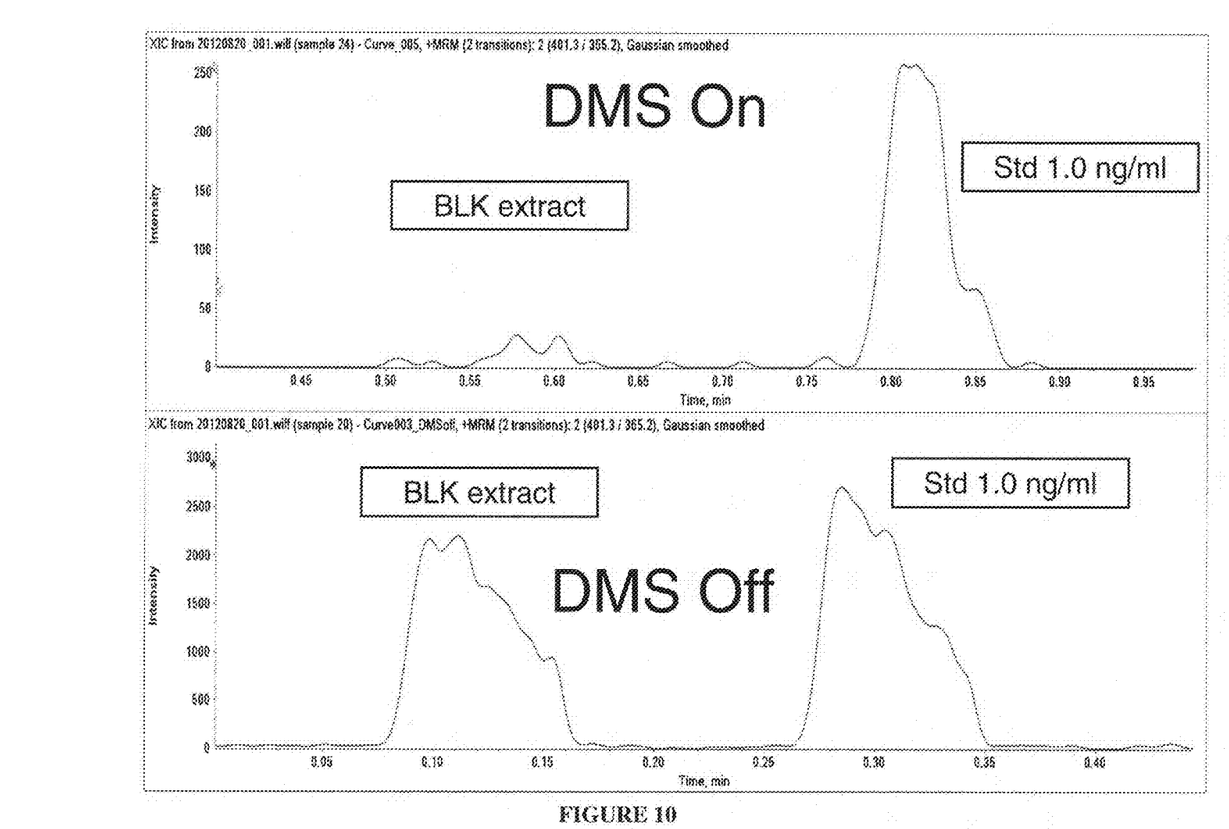
FIG. 10 shows the comparison of the interference in the blank when the LDTD source and the ion mobility device were used in tandem to analyze Vitamin D and when only the LDTD source was used and the ion mobility device was turned off in accordance with various embodiments of the applicant's teachings.

FIG. 10 shows when the LDTD source and SelexION™ ion mobility device was on and were used in tandem to analyze Vitamin D, the interference in the blank was reduced compared to when only the LDTD source was used with the differential mobility device off.

Figure 11:
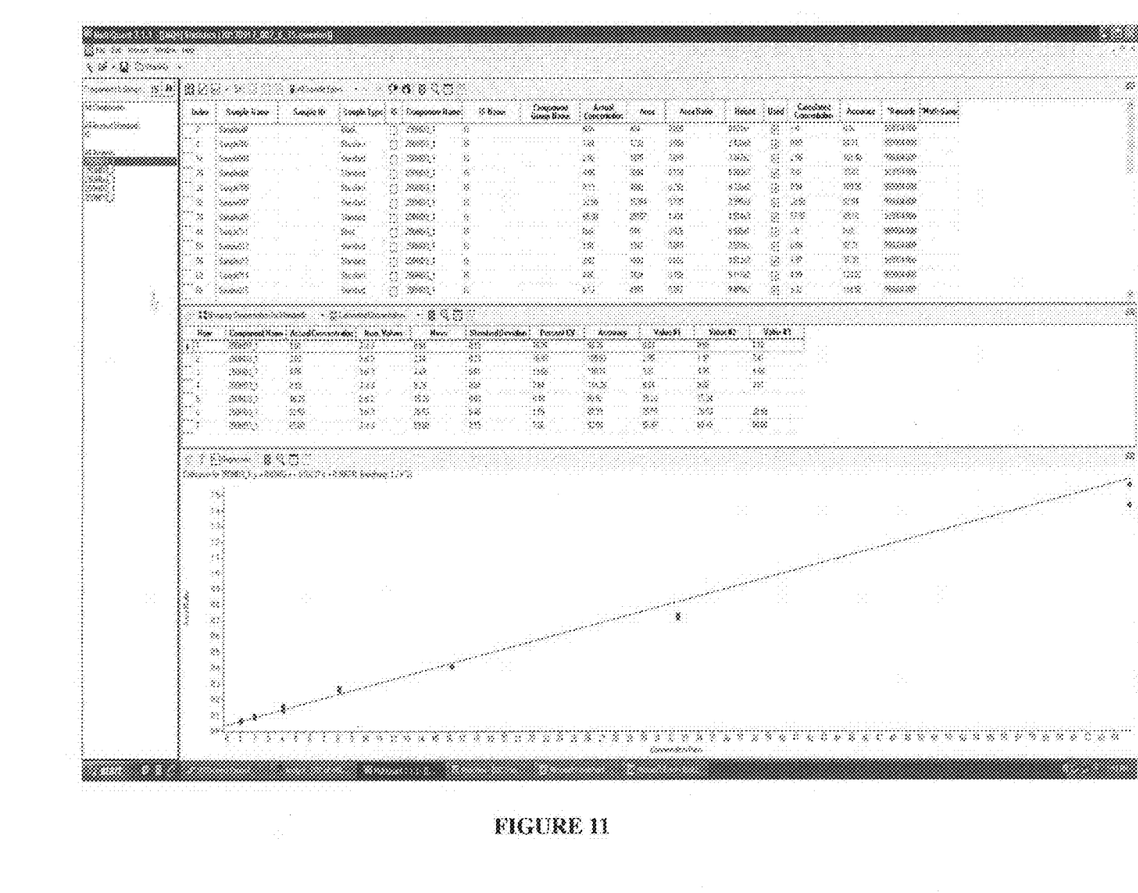
FIG. 11 shows standard curve results in accordance with various embodiments of the applicant's teachings.

FIG. 11 shows the standard curve results which show good linearity.

One skilled in the art will appreciate further features and advantages of methods and systems in accord with applicants' teachings based on the above-described embodiments. Accordingly, the applicants' disclosure is not to be limited by what has been particularly shown and described, except as indicated by the appended claims. All publications and references cited herein are expressly incorporated herein by reference in their entirety.

What is claimed is:

1. A method of quantifying an analyte in a biological sample, comprising:
    preparing a biological sample for mass spectrometric analysis,
    utilizing an ionization source to ionize at least a portion of said prepared biological sample to generate an ionized analyte flow,
    introducing said ionized analyte flow into a differential mobility spectrometer set at a compensation voltage selected to extract ionized analyte molecules from the ionized analyte flow,
    introducing an output analyte flow of the differential mobility spectrometer into a mass spectrometer to detect and quantify analyte ions in said output analyte flow;
    and wherein said ionization source comprises a diode laser to impart heat energy to said prepared biological sample to desorb at least a portion of said prepared biological sample.

2. The method of claim 1, wherein the analyte comprises testosterone.

3. The method of claim 1, wherein the analyte is selected from the group consisting of 25-OH-Vitamin D2 and 25-OH-Vitamin D3.

4. The method of claim 1, wherein said mass spectrometer comprises a tandem mass spectrometer.

5. The method of claim 4, wherein at least one precursor-product ion pair transitions having an m/z value of about 289/97, 289/109, 292/97, 401.3/365.2, 401.3/257.1, 401.3/201.1, 413.3/355.2, and 413.3/337.2 is detected.

6. The method of claim 1, wherein said compensation voltage is about 4 volts to about 14 volts.

7. The method of claim 2, wherein said testosterone is detected at a quantitation limit of about 0.1 ng/mL.

8. The method of claim 1, wherein said ionization source comprises an APCI ionizer for ionizing said desorbed biological sample.

9. The method of claim 1, wherein the biological sample is prepared without liquid chromatographic separation.

10. The method of claim 9, wherein preparing the sample comprises performing liquid-liquid extraction and drying the biological sample prior to said ionizing step.

11. The method of claim 10, further comprising utilizing the ionization source to ionize at least a portion of an additional prepared biological sample to generate an additional ionized analyte flow within about 10 seconds of ionizing said prepared biological sample.

12. A mass spectrometry system, comprising:
an ionization source having a heat source configured to apply heat to a sample to generate a desorbed sample and an ionizer for ionizing at least a portion of the desorbed sample to generate an ionized sample,
a differential mobility spectrometer in communication with the ionization source, the differential mobility spectrometer configured to receive at least a portion of the ionized sample from the ionization source and transmit ions of a selected differential mobility, and
a mass spectrometer in communication with the differential mobility spectrometer, the mass spectrometer configured to analyze the said ions of the selected differential mobility received from the differential mobility spectrometer;
wherein the heat source comprises a laser diode.

13. The system of claim 12, wherein the sample comprises testosterone.

14. The system of claim 12, wherein the sample is selected from the group consisting of 25-OH-Vitamin D2 and 25-OH-Vitamin D3.

15. The system of claim 12, wherein the ionizer comprises an atmospheric pressure chemical ionization source.

16. The system of claim 12, wherein the ionizer comprises an ultraviolet light source configured to generate a light beam for ionizing said desorbed sample by photo-ionization.

17. The system of claim 12, wherein the mass spectrometer comprises a tandem mass spectrometer.

18. A method of quantifying an analyte in a biological sample, comprising:
preparing a biological sample for mass spectrometric analysis,
utilizing an ionization source to ionize at least a portion of said prepared biological sample to generate an ionized analyte flow,
introducing said ionized analyte flow into a differential mobility spectrometer set at a compensation voltage selected to extract ionized analyte molecules from the ionized analyte flow,
introducing an output analyte flow of the differential mobility spectrometer into a mass spectrometer to detect and quantify analyte ions in said output analyte flow;
and wherein the analyte is selected from the group consisting of testosterone, 25-OH-Vitamin D2 and 25-OH-Vitamin D3.

19. The method of claim 18, wherein said mass spectrometer comprises a tandem mass spectrometer.

20. The method of claim 19, wherein at least one precursor-product ion pair transitions having an m/z value of about 289/97, 289/109, 292/97, 401.3/365.2, 401.3/257.1, 401.3/201.1, 413.3/355.2, and 413.3/337.2 is detected.

21. A method of quantifying an analyte in a biological sample, comprising:
preparing a biological sample for mass spectrometric analysis,
utilizing an ionization source to ionize at least a portion of said prepared biological sample to generate an ionized analyte flow,
introducing said ionized analyte flow into a differential mobility spectrometer set at a compensation voltage selected to extract ionized analyte molecules from the ionized analyte flow,
introducing an output analyte flow of the differential mobility spectrometer into a mass spectrometer to detect and quantify analyte ions in said output analyte flow and wherein preparing the sample comprises performing liquid-liquid extraction and drying the biological sample prior to said ionizing step and wherein the biological sample is prepared without liquid chromatographic separation.

22. The method of claim 21, further comprising utilizing the ionization source to ionize at least a portion of an additional prepared biological sample to generate an additional ionized analyte flow within about 10 seconds of ionizing said prepared biological sample.

* * * * *